United States Patent [19]

Kimura et al.

[11] Patent Number: 5,385,836
[45] Date of Patent: Jan. 31, 1995

[54] NONWOVEN FABRIC COATED WITH A MIXTURE OF SILK FIBROIN, GELATIN AND INSOLUBILIZED CHITOSAN FOR USE AS A CARRIER FOR ANIMAL CELLS

[75] Inventors: Fuminori Kimura; Shinjiro Mitsuda, both of Saitama; Yoshiaki Matsuda, Ibaraki, all of Japan

[73] Assignees: Japan Vilene Co. Ltd.; Snow Brand Milk Products, both of Tokyo, Japan

[21] Appl. No.: 885,140

[22] Filed: May 18, 1992

[30] Foreign Application Priority Data

May 17, 1991 [JP] Japan .................. 3-141348

[51] Int. Cl.⁶ .............. C12N 11/02; C12N 5/00; C12N 11/12; C12N 11/08
[52] U.S. Cl. .................. 435/177; 435/178; 435/179; 435/180; 435/240.23; 435/240.243
[58] Field of Search .............. 435/177, 178, 179, 180, 435/240.23, 240.243

[56] References Cited

U.S. PATENT DOCUMENTS

| | | | |
|---|---|---|---|
| 4,169,761 | 10/1979 | Precausta et al. | 435/235.1 |
| 4,818,291 | 4/1989 | Iwatsuki et al. | 116/124 |
| 4,999,295 | 3/1991 | Asakura et al. | 435/177 |
| 5,037,749 | 8/1991 | Findlay | 435/176 |
| 5,079,161 | 1/1992 | Mitsuda et al. | 435/176 |
| 5,173,421 | 12/1992 | Kiniwa et al. | 435/240.23 X |

FOREIGN PATENT DOCUMENTS 0318266 5/1989 European Pat. Off. .
8702703 5/1987 WIPO .

OTHER PUBLICATIONS

Leighton, J., Chemical Abstracts 23770n, vol. 81, 1974, p. 287.
Biotechnology and Bioengineering, vol. 35, No. 1, 1990, New York US pp. 66–72.
Chemical Abstracts, vol. 114, No. 21 Columbus, Ohio, US; Abstract No. 203004z, 1994.
Database WPI Week 8743, Derwent Publications Ltd., London, GB; AN 87-304278, 1987.
Database WPI Week 9121, Derwent Publications Ltd., London GB; AN 91-52421, 1991.

*Primary Examiner*—David M. Naff
*Attorney, Agent, or Firm*—Burgess, Ryan and Wayne

[57] ABSTRACT

A carrier for adhering animal cells during culturing or for immobilization of animal cells is produced by coating a porous substrate with a cell adhesive material in the form of a mixture with chitosan. In a preferred embodiment, the porous substrate is a nonwoven fabric prepared by impregnating a nonwoven fabric web with a binder resin, and the mixture contains silk fibroin, gelatin and chitosan. Coating is carried out by contacting the nonwoven fabric with a solution prepared by adding silk fibroin and gelatin to an acidic aqueous solution of chitosan to coat the nonwoven fabric, drying the coated nonwoven fabric and treating the dried nonwoven fabric with an alkali to render the chitosan insoluble.

6 Claims, 3 Drawing Sheets

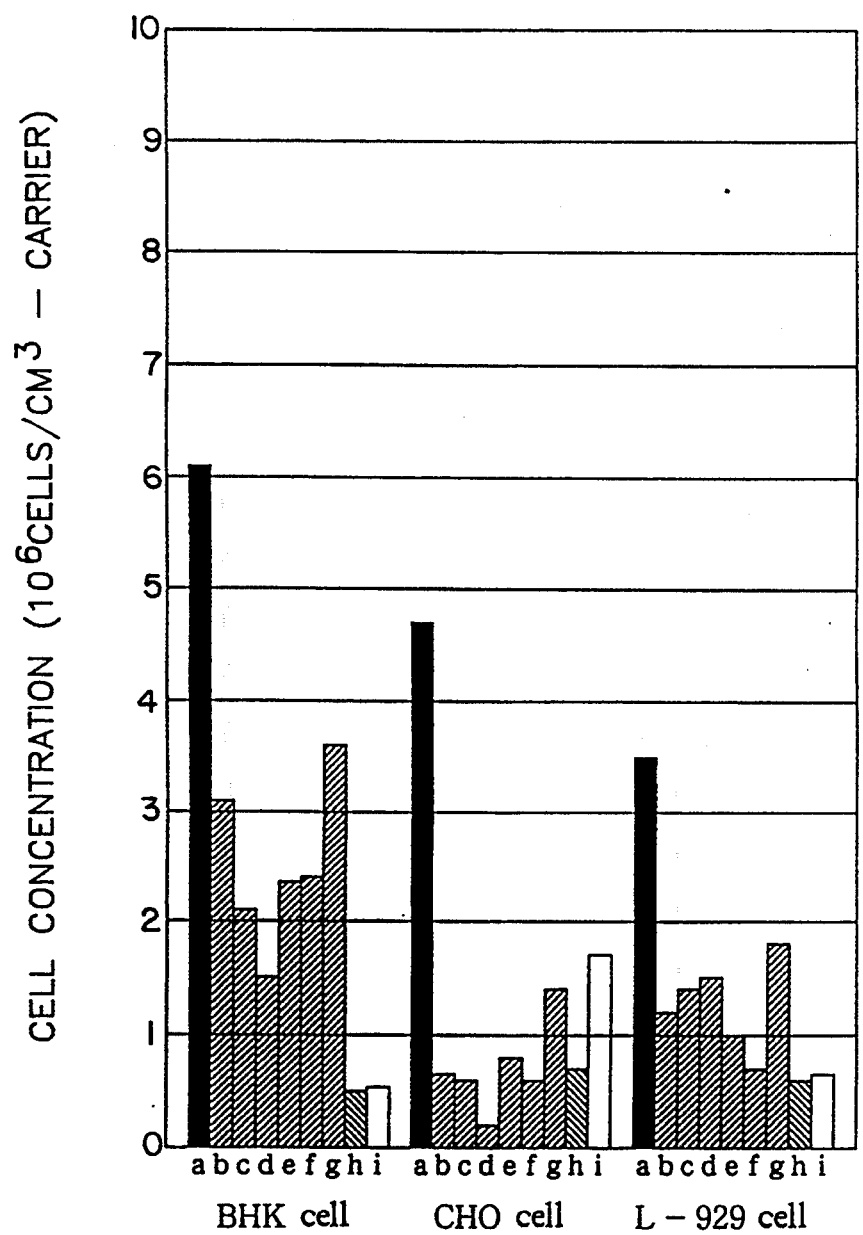
F I G. 1

NONWOVEN FABRIC COATED WITH A MIXTURE OF SILK FIBROIN, GELATIN AND INSOLUBILIZED CHITOSAN FOR USE AS A CARRIER FOR ANIMAL CELLS

BACKGROUND OF THE INVENTION

1. Field of the Invention

The present invention relates to a carrier for immobilization of animal cells, a process for manufacturing the carrier, and a method for cultivating the animal cells using the carrier.

2. Description of the Related Art

Mass production of pharmaceutically useful substances having a physiological activity is carried out by cultivating animal cells etc. The animal cells used for the cultivation include anchorage independent cells which exist in a floating state, such as blood cells and cancer cells, and anchorage dependent cells which exist adhered to a suitable carrier. It is advantageous to use floating cells (anchorage independent cells) for the efficient production of physiologically active substances. Therefore, there exists a method for selecting mutant or variant strains which can proliferate in a floating state among anchorage dependent cells to be used. Nevertheless, it is not possible to utilize the above method for all anchorage dependent cells. Accordingly, there is a demand for a suitable carrier which can be adhered to by anchorage dependent cells.

Recently, mass production of physiologically active substances is practically carried out, using recombinants, i.e., cells or microorganisms transformed by genetic recombinant techniques. When the physiologically active substances are manufactured by the recombinants, glycosylated proteins such as vaccines and antibiotics can not be obtained from recombinant microorganisms, but from recombinant animal cells. Therefore, it is considered easier to obtain useful physiologically active substances from animal cell products rather than microbial products, so it is expected that animal cells will be used in more cases. Adhesive property of animal cells, however, tends to be lowered by gene manipulation, so in this respect, development of a material superior in cell adhesion is desired.

As a carrier for immobilization of anchorage dependent cells, microcarriers having a substrate of porous beads, such as cellulose, chitosan or silane, were known. Such microcarriers had the large specific surface area per volume, and thus were considered particularly suitable for cultivation in an industrial scale. Nevertheless, the conventional microcarriers not only were prepared by complicated processes and thus expensive, but also not necessarily easy for cells to adhere to the individual beads. Further, the shearing force produced during agitation in the culture tanks damaged the cells, and careful handling was required.

Further, an immobilization Carrier prepared by coating collagen on various types of substrates was known. However, the above immobilization carrier had the defect that the sterilization treatment in an autoclave which should be carried out before immobilizing the animal cells caused flowing off of the collagen layer from the carrier and deterioration of the collagen per se, and so a reduction in the adhesive property. There existed some methods of sterilization treatment other than the above treatment in an autoclave, but these methods required special equipment or were accompanied with risk, and so were not able to be generally used.

SUMMARY OF THE INVENTION

An object of the present invention is to provide a carrier for immobilization of animal cells which can be easily adhered to by anchorage dependent cells, is inexpensive, easy to handle, and can be subjected to simple autoclave sterilization treatment Accordingly, the present invention relates to a carrier for immobilization of animal cells comprising a porous substrate, and an animal cell adhesive material carried continuously or discontinuously on an entire surface of the porous substrate in the form of a mixture with chitosan.

Further, the present invention relates to a process for manufacturing the carrier for immobilization of animal cells; comprising preparing a coating solution by adding an animal cell adhesive material to an acidic aqueous solution of chitosan; contacting a porous substrate with said coating solution; drying said coated substrate; and treating said dried substrate with an alkali to render said chitosan insoluble.

Still further, the present invention also relates to a method for cultivating animal cells; comprising adhering the animal cells to the above-mentioned carriers; and cultivating said animal cells to proliferate.

DESCRIPTION OF THE DRAWINGS

FIG. 1 is a graph showing the results of a comparison of the cell carrying capabilities of the carrier according to the present invention and the known carrier.

DESCRIPTION OF THE PREFERRED EMBODIMENTS

Figure 2:
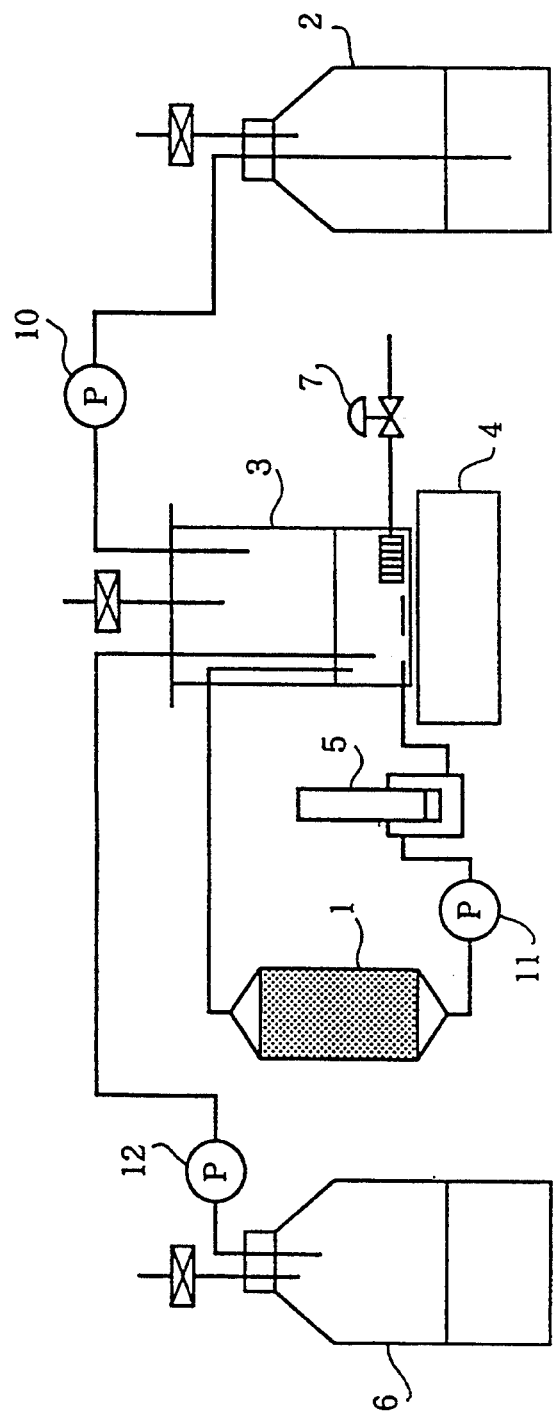
FIG. 2 is an explanatory view schematically showing the structure of a fixed bed type reactor.

The porous material which may be used as the substrate in the present invention is not particularly limited, but preferably is a hydrophilic organic porous material, for example, a nonwoven fabric, a textile fabric (woven or knitted fabric; particularly a three-dimensional textile fabric) or a foam. The foam which may be used as the substrate in the present invention is not particularly limited, but there may be mentioned a hydrophilic foam, for example, a cellulose foam or polyurethane foam.

The fabric which may be used as the substrate in the present invention mainly comprises hydrophilic fibers. Namely, a nonwoven fabric or textile fabric containing at least 50 percent of hydrophilic fibers may be used. The hydrophilic fiber is not particularly limited, but there may be mentioned, for example, regenerated cellulose fiber, polyamide fiber, protein containing fiber, and natural fiber (for example, cotton, flax, silk, or wool). Further, the hydrophilic fiber includes a modified fiber prepared by subjecting a hydrophobic fiber (for example, polyethylene, polypropylene, acrylic or urethane fiber) to any treatment imparting hydrophilicity (for example, ultraviolet irradiation or plasma treatment). The hydrophilicity imparting treatment may be subjected to the fiber or resin at any stage before the formation of the nonwoven, woven or knitted fabric and also may be carried out after the formation of the nonwoven, woven or knitted fabric.

The thickness of the hydrophilic fiber constituting the nonwoven, woven or knitted fabric is not particularly limited, but a thickness of 3 to 100 denier, particularly 10 to 100 denier, is preferred. Animal cells are generally of a size of about 10 to 20 μm and are spherical in the floating state, but flatten out when adhered to a carrier. Therefore, the fiber having a large diameter is preferable, because the cells can wrap around the fiber and flatten out thereon. If the fiber diameter is less than 3 denier, the distance between fibers becomes smaller and the cells can not enter into the nonwoven, woven or knitted fabric, and as a result the efficiency of proliferation of the cells is reduced. Further, supplement of the nutrient components of the medium and dissolved oxygen to the nonwoven, woven or knitted fabric becomes difficult. If the fiber diameter exceeds 100 denier, the surface area of the nonwoven, woven, or knitted fabric becomes smaller as a whole, and thus the efficiency of adhesion of the cells is reduced, and further the processability of the nonwoven, woven or knitted fabric is lowered.

In the present invention, it is preferable to use a nonwoven fabric which has been subjected to needle punching treatment. The needle punching treatment produces three dimensional entanglement of the constituent fibers with each other, so the cells are easily immobilized by entering inside the nonwoven fabric and the efficiency of proliferation is improved. Further, it is preferable in the present invention to use a thick woven or knitted fabric with a three dimensional woven structure or knitted structure. The fiber density of the nonwoven, woven or knitted fabric used in the present invention is preferably in a range of 0.02 to 0.1 g/cm$^3$, more preferably 0.03 to 0.07 g/cm$^3$. If the fiber density is less than 0.02 g/cm$^3$, the fabric prepared therefrom cannot retain its shape and the strength thereof is insufficient in handling, while if the fiber density is more than 0.1 g/cm$^3$, sufficient space cannot be formed in the nonwoven, woven or knitted fabric, so the cells cannot enter inside the fabric. Therefore, not only the number of cells decrease, but also the culture medium cannot sufficiently spread throughout the fabric, and as a result, the yield of the desired physiologically active substance is reduced.

In the present invention, it is possible to use a resin which is ordinarily used as a binder for a nonwoven fabric, but a hydrophilic resin is preferable so as not to inhibit the adhesion with animal cells. Further, a water-insoluble resin is preferable, because the nonwoven fabric carrying the adhered animal cells thereon is used in a culture medium. Also, it is preferable to use a resin having resistance to hot water so as to enable autoclaving treatment with an added PBS (phosphate-buffered saline). For example, polyurethane is preferable because of high adhesive properties with fibers, wettability by water, and an excellent resistance to hot water. A particularly preferable polyurethane is a polyester type which has a modulus at 100 percent of 20 kg/cm$^2$ or more when formed into a film.

The nonwoven fabric used as the porous substrate in the present invention may be prepared as in the conventional process for manufacturing a nonwoven fabric, for example, by impregnating a web mainly comprising hydrophilic fibers with the binder resin, and drying the impregnated web.

The animal cell adhesive material (i.e., the material capable of adhering animal cells) used in the present invention is selected from the group consisting of silk fibroin, bone powder, gelatin, collagen, and bivalent positive ion producing salts (in particular, bivalent positive ion producing inorganic salts). The animal cell adhesive materials are carried on the entire surface of the porous substrate in the form of a mixture with chitosan. In the specification, the expression "on the entire surface of the porous substrate" means not only the surface which forms the outside of the porous substrate, but also the surfaces inside the porous substrate. The above-mentioned mixture is carried discontinuously in a dispersed state or carried continuously on the entire surface.

Chitosan is a product (β-poly-D-glucosamine) which can be obtained by heating chitin (β-poly-N-acetyl-D-glucosamine) with a concentrated alkaline solution, or potassium fusing, and then deacetylizing. In the present invention, any chitosan may be used, but chitosan which has a deacetylization degree of 75 percent or more and has a solution viscosity of 300 to 5000 centipoise when dissolved in a 0.6 percent by weight L-lactic acid aqueous solution in an amount of 0.5 percent by weight is preferable, because a film with a good membrane strength can be formed.

Silk fibroin is converted to a polypeptide having a stable structure with a silk II type configuration when heated to around the temperature used in autoclaving treatment. A polypeptide inherently has a high biocompatibility, and further silk fibroin is converted into a stable form upon heating. Therefore, silk fibroin is preferable as the animal cell adhesive material used in the present invention.

Bone powder is a porous substance of hydroxyapatite, and there exists collagen in the pores thereof. Therefore, bone powder has high biocompatibility and superior cell adhesive properties. Further, by virtue of large specific gravity, bone powder may be used to adjust the specific gravity of the immobilization carrier according to the present invention as a whole.

Gelatin is a thermally modified collagen and is superior in cell adhesive properties. If gelatin is merely coated on a porous substrate alone, it will flow off from the substrate upon autoclaving treatment, but in the present invention the gelatin is carried on the porous substrate in the form of a mixture with chitosan and the gelatin firmly adheres thereto, and so does not flow off upon autoclaving treatment and can be used as the animal cell adhesive material in the present invention.

Further, collagen has been used as an adhesive material in conventional carriers for immobilization of animal cells. But in the prior art, collagen has merely be coated on the porous substrate alone, and thus flows off upon autoclaving treatment. In the present invention, however, collagen is included in and/or on the porous substrate in the form of a mixture with chitosan and therefore collagen is firmly adhered to the porous substrate, so will not flow off even upon autoclaving treatment and can be used as the animal cell adhesive material of the present invention.

A bivalent positive ion producing salt (in particular, a bivalent positive ion producing inorganic salt) is a compound which discharges negative ions in water to become a bivalent positive ion. For example, there may be mentioned carbonates, hydrochlorides, sulfates or phosphates of alkaline earth metals (for example, calcium or magnesium). If bivalent positive ions exist on the surface of the porous substrate, cells may easily adhere thereto, because the surfaces of cells are charged negatively. Calcium carbonate has the effect of maintaining the culture medium neutral, and so is particularly preferable.

In the present invention, the above-mentioned animal cell adhesive materials may be used alone or in the form of a mixture thereof. It is particularly preferable to use silk fibroin and/or gelatin, in view of stability against autoclaving treatment and good adhesive properties to the animal cells.

The animal cell immobilization carrier of the present invention may be prepared by adding the above-mentioned animal cell adhesive material to a 0.1 to 10 percent acidic aqueous solution of chitosan, preferably an aqueous solution of an organic acid (for example, substituted or unsubstituted aliphatic carboxylic acid, such as acetic, propionic, lactic, benzoic or glutamic acid) to produce a coating solution, applying (for example, coating, spraying, dipping, or impregnating) the coating solution to the above-mentioned porous substrate, then drying to precipitate out the chitosan, and adding an alkali, such as a dilute aqueous solution of an alkaline metal hydroxide, i.e., affecting alkaline treatment, to render the chitosan insoluble. In this manner, the animal cell adhesive material contained in the chitosan aqueous solution is firmly adhered to the entire surface of the three dimensional porous substrate with the insoluble chitosan.

If the concentration of chitosan in the chitosan acidic aqueous solution is lower than 0.1 percent, the effect aimed at by the present invention cannot be sufficiently obtained, while if the concentration is over 10 percent, the chitosan solution becomes too viscous to perform processing and to maintain sufficient solubility. The amount of chitosan carried on the substrate is not particularly limited, but preferably 0.5 to 50 g/m$^2$, more preferably 5 to 30 g/m$^2$. If the amount is less than 0.5 g/m$^2$, it becomes difficult to stably hold the animal cell adhesive material on the carrier, while if the amount is over 50 g/m$^2$, the pores of the substrate are clogged. The amount of the mixture of chitosan and the animal cell adhesive material carried on the substrate is not particularly limited. However, in the case of silk fibroin, collagen or gelatin, the amount of the mixture preferably ranges 1 to 100 g/m$^2$. If the amount is less than 1 g/m$^2$, the adhesion of the animal cells becomes insufficient, while if the amount is over 100 g/m$^2$, there is no increase observed in the number of adhered animal cells along with an increase in the amount carried. The amount of the mixture with bone powder or bivalent positive ion producing salts carried on the substrate is preferably in the range of 10 to 200 g/m$^2$. If the amount is less than 10 g/m$^2$, the adhesion of the animal cells becomes insufficient, while if the amount is over 200 g/m$^2$, it becomes difficult to stably carry the salts on the porous substrate and further there is no increase observed in the number of adhered animal cells along with an increase in the amount carried.

The carrier of the present invention may be treated in an autoclave in the presence of a PBS or a physiological saline solution. The carrier of the present invention may be used in the form of relatively large clumps or may be used after divided into relatively small pieces.

The animal cells which can be immobilized on and/or in the carrier of the present invention are not particularly limited, but for example there may be mentioned cells used as host cells in genetic recombination, such as BHK, L929 or CHO (Chinese hamster ovary), and normal cells, such as IMR-90 cells.

The immobilization may be carried out in the same manner as in conventional animal cell immobilization. For example, a suspension of animal cells may be passed through a column filled with the animal cell immobilization carriers of the present invention, or the animal cell immobilization carriers of the present invention may be dipped in a suspension of animal cells.

The animal cell immobilization carrier of the present invention may be used as a carrier for cultivation of animal cells in a floating type or filling type cultivation apparatus. In the case of a floating type culture apparatus, for example, the animal cell immobilization carrier of the present invention is divided into blocks (about 5 mm×5 mm×5 mm) or cylinders (about 6 mm diameter). The carriers are dipped in the animal cell suspension, thereby immobilizing the animal cells. The carriers with the animal cells immobilized thereon are agitated or kept moving, and the cultivation is performed in a floating state. On the other hand, in the case of the filling type culture apparatus, for example, the animal cell immobilization carriers of the present invention are laid in the culture tank in a sheet form or packed in piece form and then the animal cell suspension is passed therethrough so as to immobilize the animal cells. After the animal cells are immobilized, the culture medium is passed and circulated in the culture tank and the animal cells are cultivated. In either case, the physiologically active substance aimed at is secreted from the cultivated animal cells, so the resulting products may be separated and purified. Further, the proliferated cells may grow while adhering on the carrier.

EXAMPLES

The present invention now will be further illustrated by, but by no means limited to, the following Examples.

Example 1

A rayon fiber web (170 g/m$^2$; average fiber diameter=15 denier; and average fiber length=76 mm) was needle-punched (needle density=200 needles/cm$^2$) to obtain a needle-punched felt. A binder solution containing 20 parts by weight of polyurethane emulsion (solids content=35 percent) (Melusi-589: Toyo Polymer) and 0.5 part by weight of an epoxy cross-linking agent (AD-C-65: Toyo Polymer) and an amount of distilled water to make 100 parts by weight the whole was evenly impregnated into the needle-punched felt by squeezing through a slit of a width of 0.7 mm with a stainless steel mangle, and thereafter cross-linked and dried at 150° C. (amount of binder=25 g/m$^2$).

Then, a coating solution containing 70 parts by weight of a 1 percent chitosan solution [prepared by dissolving 1 g of chitosan (deacetylization rate of 85 to 95 percent: Wako Junyaku) in 98.4 g of distilled water and 0.6 g of L-lactic acid (Wako Junyaku) at 58° C.], 20 parts by weight of a 3 percent fibroin aqueous solution, and 10 parts by weight of an 8 percent gelatin aqueous solution was evenly impregnated into the above-mentioned urethane-impregnated needle-punched felt by squeezing through a slit of a width of 0.8 mm with a stainless steel mangle. The impregnated felt was dried at 150° C., then treated with a 4 percent NaOH aqueous solution to render the chitosan insoluble, then was rinsed and once again dried at 150° C. to obtain the carrier (weight per unit area=270 g/m$^2$; thickness=3.0 mm).

Example 2: Silk Fibroin

The procedure described in Example 1 was repeated, except that as the coating solution, a solution containing 70 parts by weight of a 1 percent chitosan solution and 30 parts by weight of a 3 percent fibroin aqueous solution was used to obtain the carrier (weight per unit area=265 g/m$^2$; thickness=3.2 mm).

Example 3: Bone Powder

The procedure described in Example 1 was repeated, except that as the coating solution, a solution containing 5 parts by weight of bone powder and 5 parts by weight of distilled water was used instead of the 10 parts by weight of an 8 percent gelatin aqueous solution to obtain the carrier (weight per unit area=317 g/m$^2$; thickness=2.6 mm).

Example 4: Collagen

The procedure described in Example 1 was repeated, except that as the coating solution, a solution containing 2 parts by weight of collagen powder and 8 parts by weight of distilled water was used instead of the 10 parts by weight of an 8 percent gelatin aqueous solution to obtain the carrier (weight per unit area=245 g/m$^2$; thickness of 3.1 mm).

Example 5: Salt

The procedure described in Example 1 was repeated, except that as the coating solution, a solution containing 10 parts by weight of calcium carbonate was used instead of the 10 parts by weight of an 8 percent gelatin aqueous solution to obtain the carrier (weight per unit area=230 g/m$^2$; thickness=2.2 mm).

Comparative Example 1

The procedure described in Example 1 was repeated to prepare the urethane impregnated needle-punched felt.

Thereafter, a coating solution containing 69.5 parts by weight of a 10 percent aqueous solution of completely saponified polyvinyl alcohol (PVA-117H: Kurarey), 0.5 part by weight of 1,3-dimethylurea, 20 parts by weight of a 3 percent fibroin aqueous solution, and 10 parts by weight of an 8 percent gelatin aqueous solution was used to obtain a carrier (weight per unit area=250 g/m$^2$; thickness=2.8 mm) by the procedure described in Example 1.

Comparative Example 2

The procedure described in Example 1 was repeated to prepare the urethane impregnated needle-punched felt.

Then, a coating solution containing 20 parts by weight of a polyurethane emulsion (solids content=35 percent) (Melusi-589: Toyo Polymer), 0.5 part by weight of an epoxy type crosslinking agent (AD-C-65: Toyo Polymer), 30 parts by weight of a 10 percent aqueous solution of completely saponified polyvinyl alcohol (PVA117H: Kurarey), 0.5 part by weight of 1,3-dimethylurea, 20 parts by weight of a 3 percent fibroin aqueous solution, and 10 parts by weight of an 8 percent gelatin aqueous solution was used to obtain a carrier (weight per unit area=280 g/m$^2$; thickness=2.8 mm) by the procedure described in Example 1.

Comparative Example 3

The procedure described in Example 1 was repeated, except that as the binder solution, the coating solution described in Comparative Example 2 was used. The needle punched felt (weight per unit area=250 g/m$^2$; thickness=2.8 mm) prepared by impregnating the binder solution (coating solution) was used for the evaluation of the carrier as mentioned below.

Test Examples 1–4 (Method of Evaluation of Carrier)

The carriers prepared in the above-mentioned Examples 1 to 5 and Comparative Examples 1 to 3 were evaluated as to the autoclaving treatment characteristics, cell carrying capability, and cultivation effect thereof by the following methods:

Test Example 1: Autoclaving Treatment Characteristic

Twenty sample pieces (6 mm×6 mm) were prepared by cutting nonwoven fabric. The sample pieces were placed in a 100 ml tall beaker, then 40 ml of distilled water was added, and the beaker was sealed with an aluminum foil. The samples were autoclaved at 121° C. for 15 minutes, and then, the degree of turbidity of the distilled waster was evaluated. Further, a stirring rod coated with teflon (diameter=8 mm; length=30 mm) was placed in the beaker, the whole in the beaker was stirred with a magnetic stirrer at 200 rpm for 24 hours, and the degree of unraveling of the fibers of the nonwoven fabric was observed. The results are shown in Table 1.

TABLE 1

| Evaluation item | Examples | | | | | C. Ex.* | | |
|---|---|---|---|---|---|---|---|---|
|  | 1 | 2 | 3 | 4 | 5 | 1 | 2 | 3 |
| Turbidity due to autoclave | o | o | o | o | o | x | x | x |
| Unraveling due to agitation | o | o | o | o | o | o | o | x |
| Overall evaluation | o | o | o | o | o | x | x | x |

Note:
"C. Ex" means Comparative Examples, "o" means good and "x" means poor.

Test Example 2: Cell Carrying Capability

Nonwoven fabric samples (15 mm×15 mm) were placed in centrifugation tubes. To each of the centrifugation tubes, 10 ml of PBS solution was added, then sterilization was performed at a temperature of 120° C. for 20 minutes, and 10 ml of proliferation medium (prepared by adding 10 percent bovine serum and 10 percent tryprose phosphate broth to DMEM) was added to replace the PBS solution. This procedure was repeated two times. The examined nonwoven fabric pieces were transferred to 12 well plate (made by Corning) and about 2 ml portions of BHK cell suspension (1×10$^5$ cells/ml) were added. Thereafter, the plate was allowed to stand in an incubator at 37° C. in air containing 5 percent carbon dioxide for about 4 hours. Then, a medium prepared by adding 10 percent bovine serum and 10 percent tryptose phosphate broth to a DMEM (Dulbecco's Modified Eagle Medium: GIBCO) was added to the plate and cultivation was performed for three days. The pieces of the nonwoven fabric were observed under a microscope (200 x) to evaluate the adhesion of the animal cells. Then, the animal cells were removed by trypsin treatment from the examined nonwoven fabric pieces and the number of the removed cells was counted by a blood cell calculator. In the nonwoven fabric sample of Example 1, the number was $4.2 \times 10^6$ cells/cm$^3$, in the nonwoven fabric sample of Comparative Example 1, the number was $0.04 \times 10^6$ cells/cm$^3$, and in the nonwoven fabric sample of Comparative Example 2, the number was $0.06 \times 10^6$ cells/cm$^3$.

Test Example 3: Comparison of Cell Carrying Capability of Carrier of Present Invention and Known Carrier As the known carriers, a microcarrier (made by Asahi Chemical Industry) of porous cellulose, six types of cellulose foam [made by Sakai Engineering, Cellsnow (trade name)], and a microcarrier of porous silane (made by Schott) were prepared.

Five small pieces of the carrier prepared in Example 1 and cut into sizes of a diameter of 6 mm, 0.2 g of the porous cellulose microcarrier, 0.2 g of each of the cellulose foams, and 1 g of the porous silane microcarrier were placed into centrifugation tubes, respectively. To each of the centrifugation tubes, 10 ml of PBS solution was added, then sterilization was performed at a temperature of 120° C. for 20 minutes, and 10 ml of proliferation medium (prepared by adding 10 percent bovine serum and 10 percent tryptose phosphate broth to DMEM) was added to replace the PBS solution. This procedure was repeated two times.

Then, BHK cells (ATCC CCL10), CHO cells (ATCC CCL61), and L-929 cells (ATCC CCL1) were inoculated on the carriers in an amount of $5 \times 10^5$ cells per cm$^3$ of the carrier, and the cells were incubated in a 5 percent $CO_2$ incubator. After 24 hours, the same proliferation medium as mentioned above was added to make the total amount 8 ml. On the fifth day of cultivation, the carriers were washed with PBS solution, then the number of the cells were counted by a trypsin treatment and the cell numbers per unit volume were found. The results are shown in FIG. 1. In FIG. 1, a to i mean the following carriers:

a: Carrier of the present invention (nonwoven fabric of Example 1)
b: Cellulose foam (Sakai Engineering: Cellsnow CX-N)
c: Cellulose foam (Sakai Engineering: Cellsnow CX-K)
d: Cellulose foam (Sakai Engineering: Cellsnow EX-C)
e: Cellulose foam (Sakai Engineering: Cellsnow EX-T)
f: Cellulose foam (Sakai Engineering: Cellsnow EX-P)
g: Cellulose foam (Sakai Engineering: Cellsnow EX-G)
h: Porous cellulose microcarrier (Asahi Chemical Industry: EX-K)
i: Porous silane microcarrier (Schott)

As shown in FIG. 1, regarding the BHK cells, the number was $6.1 \times 10^6$ cells/cm$^3$ on the carrier of Example 1, while it was 0.5 to $3.6 \times 10^6$ cells/cm$^3$ on the known carrier. Regarding the CHO cells, the number was $4.7 \times 10^6$ cells/cm$^3$ on the carrier of Example 1, while it was 0.2 to $1.7 \times 10^6$ cells/cm$^3$ on the known carrier. Further, regarding the L-929 cells, the number was $3.5 \times 10^6$ cells/cm$^3$ on the carrier of Example 1, while it was 0.6 to $1.8 \times 10^6$ cells/cm$^3$ on the known carrier.

When the state of adhesion of the cells was observed under a microscope (200 x), the cells were proliferated not only on the surface of the carrier of Example 1, but inside thereof as well, while in the case of the cellulose foams, the number of adhered cells was small. Regarding the porous cellulose microcarrier and the porous silane microcarrier, not only the number of adhered cells was small, but also the diameter of the pores and the size of the cells were about the same, so no cell adhered in the pores was seen.

Test Example 4: Cultivation Using Fixed Bed Type Reactor

Using a fixed bed type culture apparatus, a culture experiment of adhesive animal cells was performed. FIG. 2 is an explanatory view showing schematically the apparatus used in the test.

The animal cell immobilization carrier prepared in Example 1 was cut into pieces of a-size of a diameter of 6 mm and then about 950 pieces of the carrier were filled into a filling tank 1. A PBS suspension (90 ml) of BHK cells (ATCC CCL10) of a concentration of $30 \times 10^4$ cells/ml was supplied from the top of the filling tank 1 to inoculate the BHK cells in the carriers, and then the whole was allowed to stand and perform cultivation for about 4 hours so as to stably adhere the cells on the carrier.

Thereafter, perfusion cultivation was carried out. In the cultivation, a fresh culture medium (prepared by adding 10 percent bovine serum and 10 percent tryprose phosphate broth to DMEM) containing glucose was continuously fed from the culture medium storage tank 2 into the circulation tank 3 by a pump 10 and was stirred and mixed with a culture medium containing the product by a stirrer 4 in the circulation tank 3. The resulting mixture medium was sent through the oxygen electrodes 5 by the pump 11 to the filling layer 1 and came into contact with the BHK cells immobilized on the carrier. In this manner, the BHK cells were proliferated and a substance was produced. The culture medium containing the product was returned to the circulation tank 3, where the medium was stirred and mixed with a fresh culture medium by the stirrer 4 in the circulation tank 3 and continuously harvested in the harvest tank 6 by the pump 12 from the circulation tank 3. Namely, in this apparatus, a fresh culture medium can be continuously supplied and products can be continuously harvested. Oxygen was supplied from a solenoid valve 7 to the circulation tank 3 so as to promote dissolution in the culture medium. The solenoid valve 7 and the oxygen electrode 5 are connected by a suitable means (not shown), and the amount of the oxygen supplied was controlled in accordance with the oxygen concentration detected by the oxygen electrode 5.

Figure 3:
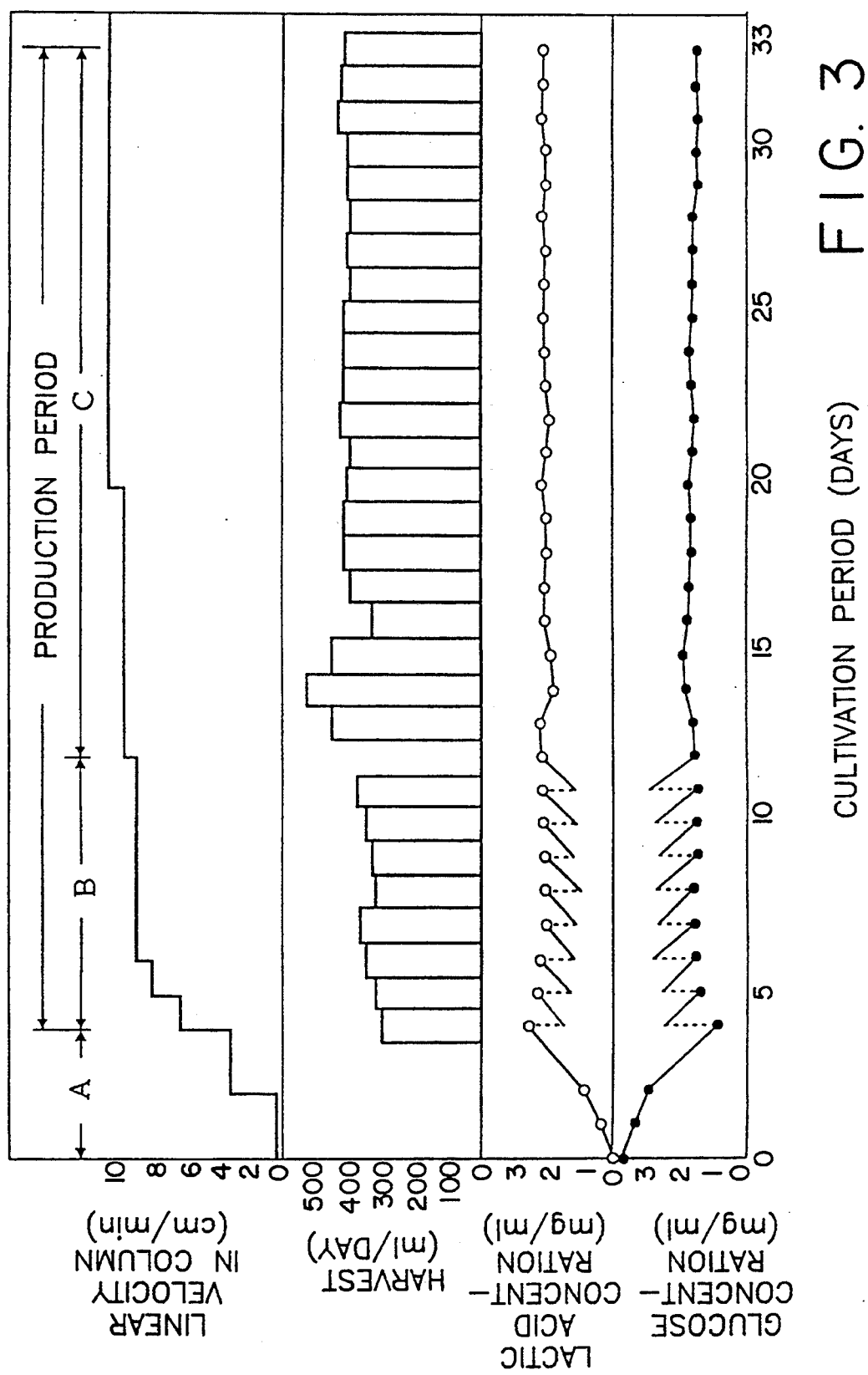
FIG. 3 is a graph showing the results of continuous perfusion cultivation.

FIG. 3 shows the changes over time of the linear velocity in the filling layer 1, the amount of culture medium from the circulation tank 3 to the harvest tank 6, the concentration of glucose in the culture medium in the circulation tank 3, and the concentration of the lactic acid (a waste product of animal cells). Batch cultivation was performed from the start of the cultivation to the fourth day (A in FIG. 3), repeated batch production was performed in the eight days from the fifth day to the 12th day (B in FIG. 3). Further, continuous perfusion cultivation was performed in the 21 days from the 13th day to the 33rd day (C in FIG. 3). The amount of the culture medium harvested and the amount of the fresh medium supplied during the period of production from the fifth day were adjusted so that the concentration of glucose in the circulation tank 3 became about 1.5 mg/ml. Namely, the fresh culture medium was supplied at the speed shown in FIG. 3 from the medium storage tank 2 to the circulation tank 3 so as to give a concentration of glucose in the culture medium in the circulation tank 3 of about 1.5 mg/ml. Simultaneously, the same amount of culture medium was harvested to the harvest tank 6.

During the above continuous perfusion cultivation, the concentration of glucose, the concentrate of lactic acid, and the amount of culture medium harvested were stable and there was little detachment of the cells, showing that the cells were immobilized on the carrier in a state maintaining their activity stably for a long period. Further, according to the above method, the method of inoculation of the animal cells in the immobilization carrier was also convenient and reliable.

In the carrier for immobilization of animal cells according to the present invention, an animal cell adhesive material having excellent adhesion with animal cells is included in a state firmly adhered to the entire surface of the porous substrate in the form of a mixture with insoluble chitosan, so will not flow off even if autoclaving sterilization treatment is performed in the presence of an aqueous solution of the medium and is resistant to degeneration due to heat.

Further, since the animal cell adhesive material is adhered dispersed in a three-dimensional porous substrate, the efficiency of adhesion of the animal cells is good and the volume of adhesion of the animal cells is large. Therefore, it is possible to efficiently make animal cells adhere to it from a low concentration animal cell suspension and further it is possible to hold and cultivate a large amount of animal cells. Further, the animal cell immobilization carrier of the present invention is made of hydrophilic materials, so the compatibility with animal cells is good.

Although the present invention has been described with reference to specific embodiments, various changes and modifications obvious to those skilled in the art are deemed to be within the spirit, scope and concept of the invention.

We claim:

1. A carrier for immobilization of animal cells comprising
   (a) a nonwoven fabric prepared by impregnating a nonwoven fabric web with a binder resin, and
   (b) a coating on said nonwoven fabric of a mixture containing silk fibroin, gelatin, and insolubilized chitosan, said mixture being present on at least some of the surface of said nonwoven fabric in an amount of 1 to 100 g/m$^2$, and wherein said mixture is coated on said nonwoven fabric by contacting said nonwoven fabric with a solution prepared by adding silk fibroin and gelatin to an acidic aqueous solution of chitosan, to coat said nonwoven fabric, drying said coated nonwoven fabric, and treating said dried nonwoven fabric with an alkali to render said chitosan insoluble.

2. A carrier according to claim 1, wherein said nonwoven fabric contains at least 50% by weight of hydrophilic fibers.

3. A carrier according to claim 1, wherein said nonwoven fabric web is a needle-punched felt.

4. A method for manufacturing a carrier for immobilization of animal cells; comprising the steps of:
   preparing a coating solution by adding silk fibroin and gelatin to an acidic aqueous solution of chitosan;
   contacting a nonwoven fabric prepared by impregnating a nonwoven fabric web with a binder resin, with said coating solution to coat said nonwoven fabric;
   drying said coated nonwoven fabric; and
   treating said dried nonwoven fabric with an alkali to render said chitosan insoluble.

5. A method for cultivating animal cells; comprising culturing said animal cells while adhered to a carrier, said carrier comprising
   (a) a nonwoven fabric prepared by impregnating a nonwoven fabric web with a binder resin, and
   (b) a coating on said nonwoven fabric of a mixture containing silk fibroin, gelatin, and insolubilized chitosan, said mixture being present on at least some of the surface of said nonwoven fabric in an amount of 1 to 100 g/m$^2$, and wherein said mixture is coated on said nonwoven fabric by contacting said nonwoven fabric with a solution prepared by adding silk fibroin and gelatin to an acidic aqueous solution of chitosan, to coat said nonwoven fabric, drying said coated nonwoven fabric, treating said dried nonwoven fabric with an alkali to render said chitosan insoluble; and cultivating said animal cells to cause proliferation.

6. A method for the immobilization of animal cells on a carrier which comprises bringing the animal cells into contact with a carrier to bind said the cells to the carrier, said carrier comprising
   (a) a nonwoven fabric prepared by impregnating a nonwoven fabric web with a binder resin, and
   (b) a coating on said nonwoven fabric of a mixture containing silk fibroin, gelatin, and insolubilized, chitosan, said mixture being present on at least some of the surface of said nonwoven fabric in an amount of 1 to 100 g/m$^2$, and wherein said mixture is coated on said nonwoven fabric by contacting said nonwoven fabric with a solution prepared by adding silk fibroin and gelatin to an acidic aqueous solution of chitosan to coat said nonwoven fabric, drying said coated nonwoven fabric, and treating said dried nonwoven fabric with an alkali to render said chitosan insoluble.

* * * * *